United States Patent

Naya

[11] Patent Number: 5,917,607
[45] Date of Patent: Jun. 29, 1999

[54] SURFACE PLASMON SENSOR FOR MULTIPLE CHANNEL ANALYSIS

[75] Inventor: Masayuki Naya, Kanagawa-ken, Japan

[73] Assignee: Fuji Photo Film Co., Ltd., Kanagawa-Ken, Japan

[21] Appl. No.: 08/847,359

[22] Filed: Apr. 24, 1997

[30] Foreign Application Priority Data

Apr. 25, 1996 [JP] Japan ................................. 8-105301
Apr. 30, 1996 [JP] Japan ................................. 8-109365

[51] Int. Cl.⁶ .......................................................... G01J 3/30
[52] U.S. Cl. ................................................ 356/445; 356/318
[58] Field of Search ....................................... 356/445, 318

[56] References Cited

U.S. PATENT DOCUMENTS

| | | | |
|---|---|---|---|
| 4,889,427 | 12/1989 | Van Veen et al. | 356/445 |
| 5,023,053 | 6/1991 | Finlan | 356/445 |
| 5,055,265 | 10/1991 | Finlan | 356/445 |
| 5,064,619 | 11/1991 | Finlan | 356/445 |
| 5,313,264 | 5/1994 | Ivarsson et al. | 356/445 |
| 5,485,277 | 1/1996 | Foster | 356/445 |
| 5,492,840 | 2/1996 | Malmqvist et al. | 356/445 |

FOREIGN PATENT DOCUMENTS 6-167443  6/1994  Japan .

*Primary Examiner*—Robert H. Kim
*Attorney, Agent, or Firm*—Sughrue, Mion, Zinn, Macpeak & Seas, PLLC

[57] ABSTRACT

A surface plasmon sensor includes a prism, a metal film which is formed on one face of the prism and is brought into contact with a sample, a light source emitting a light beam, an optical system which causes the light beam to enter the prism so that various angles of incidence of the light beam to the interface between the prism and the metal film can be obtained, and a photodetector which is able to detect the intensity of the light beam reflected in total reflection from the interface for the various angles of incidence. A light deflector deflects the light beam so that the light beam impinges upon the interface between the prism and the metal film in a plurality of different positions in sequence.

8 Claims, 4 Drawing Sheets

SURFACE PLASMON SENSOR FOR MULTIPLE CHANNEL ANALYSIS

BACKGROUND OF THE INVENTION

1. Field of the Invention

This invention relates to a surface plasmon sensor for quantitatively analyzing a material in a sample utilizing generation of surface plasmon, and more particularly to a surface plasmon sensor which can carry out such analyses on a plurality of samples at one time.

2. Description of the Related Art

In metal, free electrons vibrate in a group to generate compression waves called plasma waves. The compression waves generated in a metal surface are quantized into surface plasmon.

There have been proposed various surface plasmon sensors for quantitatively analyzing a material in a sample utilizing a phenomenon that such surface plasmon is excited by light waves. Among those, one employing a system called "Kretschmann configuration" is best known. See, for instance, Japanese Unexamined Patent Publication No. 6(1994)-167443.

The plasmon sensor using the Kretschmann configuration basically comprises a prism, a metal film which is formed on one face of the prism and is brought into contact with a sample, a light source emitting a light beam, an optical system which causes the light beam to enter the prism so that various angles of incidence of the light beam to the interface between the prism and the metal film can be obtained, and a photodetector means which is able to detect the intensity of the light beam reflected in total reflection from the interface for the various angles of incidence.

In order to obtain various angles of incidence of the light beam to the interface, a relatively thin incident light beam may be caused to impinge upon the interface while deflecting the incident light beam, or a relatively thick incident light beam may be caused to converge on the interface so that components of the incident light beam impinge upon the interface at various angles. In the former case, the light beam which is reflected from the interface at an angle which varies as the incident light beam is deflected may be detected by a photodetector which is moved in synchronization with deflection of the incident light beam or by an area sensor extending in the direction in which reflected light beam is moved as a result of deflection. In the latter case, components of light reflected from the interface at various angles may be detected by an area sensor.

In such a plasmon sensor, when a light beam impinges upon the metal film at a particular angle of incidence θsp not smaller than the angle of total internal reflection, evanescent waves having an electric field distribution are generated in the sample in contact with the metal film and surface plasmon is excited in the interface between the metal film and the sample. When the wave vector of the evanescent waves is equal to the wave number of the surface plasmon and wave number matching is established, the evanescent waves and the surface plasmon resonate and light energy is transferred to the surface plasmon, whereby the intensity of light reflected in total reflection from the interface between the prism and the metal film sharply drops.

When the wave number of the surface plasmon can be known from the angle of incidence θsp at which the phenomenon takes place, the dielectric constant of the sample can be obtained. That is, $$Ksp(\varpi) = \frac{\varpi}{c} \sqrt{\frac{\epsilon_m(\varpi)\epsilon_s}{\epsilon_m(\varpi) + \epsilon_s}}$$

wherein Ksp represents the wave number of the surface plasmon, ω represents the angular frequency of the surface plasmon, c represents the speed of light in a vacuum, and εm and εs respectively represent the dielectric constants of the metal and the sample.

When the dielectric constant εs of the sample is known, the concentration of a specific material in the sample can be determined on the basis of a predetermined calibration curve. Accordingly, a specific component in the sample can be quantitatively analyzed by detecting the angle of incidence θsp at which the intensity of light reflected in total reflection from the interface between the prism and the metal film sharply drops.

There has been a demand for carrying out analyses on a plurality of samples at one time in order to increase the working efficiency. The demand may be satisfied by a multiple channel system in which a light beam emitted from a single light source is divided into a plurality of light beams and the plurality of light beams are caused to simultaneously impinge upon the interface between the prism and the metal film.

However this approach is disadvantageous in that the amount of light beam can fluctuate from channel to channel, which results in an analyzing error. Further the number of channels cannot be so large in order to ensure a sufficient amount of light for each channel. When the amount of light for each channel is insufficient, the S/N ratio of light detecting signals deteriorates and the analyzing accuracy deteriorates.

SUMMARY OF THE INVENTION

In view of the foregoing observations and description, the primary object of the present invention is to provide a surface plasmon sensor in which a plurality of samples can be analyzed at one time with a high accuracy.

In accordance with a first embodiment of the present invention, there is provided a surface plasmon sensor comprising a prism, a metal film which is formed on one face of the prism and is brought into contact with a sample, a light source emitting a light beam, an optical system which causes the light beam to enter the prism so that various angles of incidence of the light beam to the interface between the prism and the metal film can be obtained, and a photodetector means which is able to detect the intensity of the light beam reflected in total reflection from the interface for the various angles of incidence, wherein the improvement comprises a light deflector means which deflects the light beam so that the light beam impinges upon the interface between the prism and the metal film in a plurality of different positions in sequence.

It is preferred that the optical system be arranged so that the light beam reflected in total reflection from the interface between the prism and the metal film is condensed in a predetermined position irrespective of the position where the incident light beam impinges upon the interface.

In the surface plasmon sensor in accordance with the first aspect of the present invention, the incident light beam impinges upon the interface between the prism and the metal film in a plurality of different positions in sequence, and accordingly, by placing a plurality of samples in contact with a plurality of portions of the metal film corresponding to the positions where the incident light beam impinges upon the metal film, analyses of a plurality of samples can be effected in a short time at one time.

Further since the analyses in a plurality of channels are effected by use of a single light beam, the amount of light beam does not fluctuate from channel to channel, which ensures a high analyzing accuracy.

Further since the amount of light beam for each channel can be sufficient unlike the case where a single light beam is divided into a plurality of light beams, the number of channels can be substantially increased.

Further since the light source emitting a single light beam is less expensive as compared with a light source emitting a plurality of light beams, the surface plasmon sensor for a multiple channel analysis can be produced at lower cost than that for a surface plasmon sensor for a multiple channel analysis using a light source emitting a plurality of light beams.

When the optical system is arranged so that the light beam reflected in total reflection from the interface between the prism and the metal film is condensed in a predetermined position irrespective of the position where the incident light beam impinges upon the interface, the photodetector means may be one in number, which is advantageous from the viewpoint of cost.

In accordance with a second aspect of the present invention, a semiconductor laser array having a plurality of light emitting portions is used as the light source and a multiple channel analysis is realized by use of a plurality of light beams emitted from the semiconductor laser array.

That is, in accordance with the second aspect of the present invention, there is provided a surface plasmon sensor comprising a prism, a metal film which is formed on one face of the prism and is brought into contact with a sample, a semiconductor laser array which has a plurality of light emitting portions each emitting a light beam, an optical system which causes the light beams emitted from the semiconductor laser array to enter the prism so that various angles of incidence to the interface between the prism and the metal film can be obtained for each of the light beams, and a photodetector means which is able to detect the intensity of each of the light beams reflected in total reflection from the interface for the various angles of incidence.

In the surface plasmon sensor in accordance with the second aspect of the present invention, analyses of a plurality of samples can be effected simultaneously or substantially simultaneously by use of a plurality of light beams emitted from a semiconductor laser array.

Further since the light beam used in each channel is emitted from each of the light emitting portions of the semiconductor laser array, a sufficient amount of light can be ensured for each of the channels, unlike the case where the light beam used in each channel is obtained by dividing a single light beam into a plurality of light beams, whereby a high analyzing accuracy can be obtained.

In one embodiment of the second aspect of the present invention, the semiconductor laser array is driven so that light beams are emitted simultaneously from the light emitting portions of the semiconductor laser array, the optical system is arranged to condense the plurality of light beams reflected from the interface between the prism and the metal film in different positions, and the photodetector means has a plurality of light receiving portions each of which discretely receives one of the condensed light beams.

In this embodiment, the plurality of light beams emitted from the semiconductor laser array are used in parallel and analyses in the plurality of channels can be effected simultaneously.

In another embodiment of the second aspect of the present invention, the semiconductor laser array is driven so that light beams are emitted in sequence from the light emitting portions of the semiconductor laser array at time intervals, the optical system is arranged to condense the plurality of light beams reflected from the interface between the prism and the metal film in the same position and the photodetector means has a light receiving portion common to the plurality of the condensed light beams.

In this embodiment, though analyses in the plurality of channels cannot be effected completely simultaneously, the photodetector means may be simple in structure and accordingly the surface plasmon sensor can be produced at relatively low cost.

DESCRIPTION OF THE PREFERRED EMBODIMENTS

Figure 1:
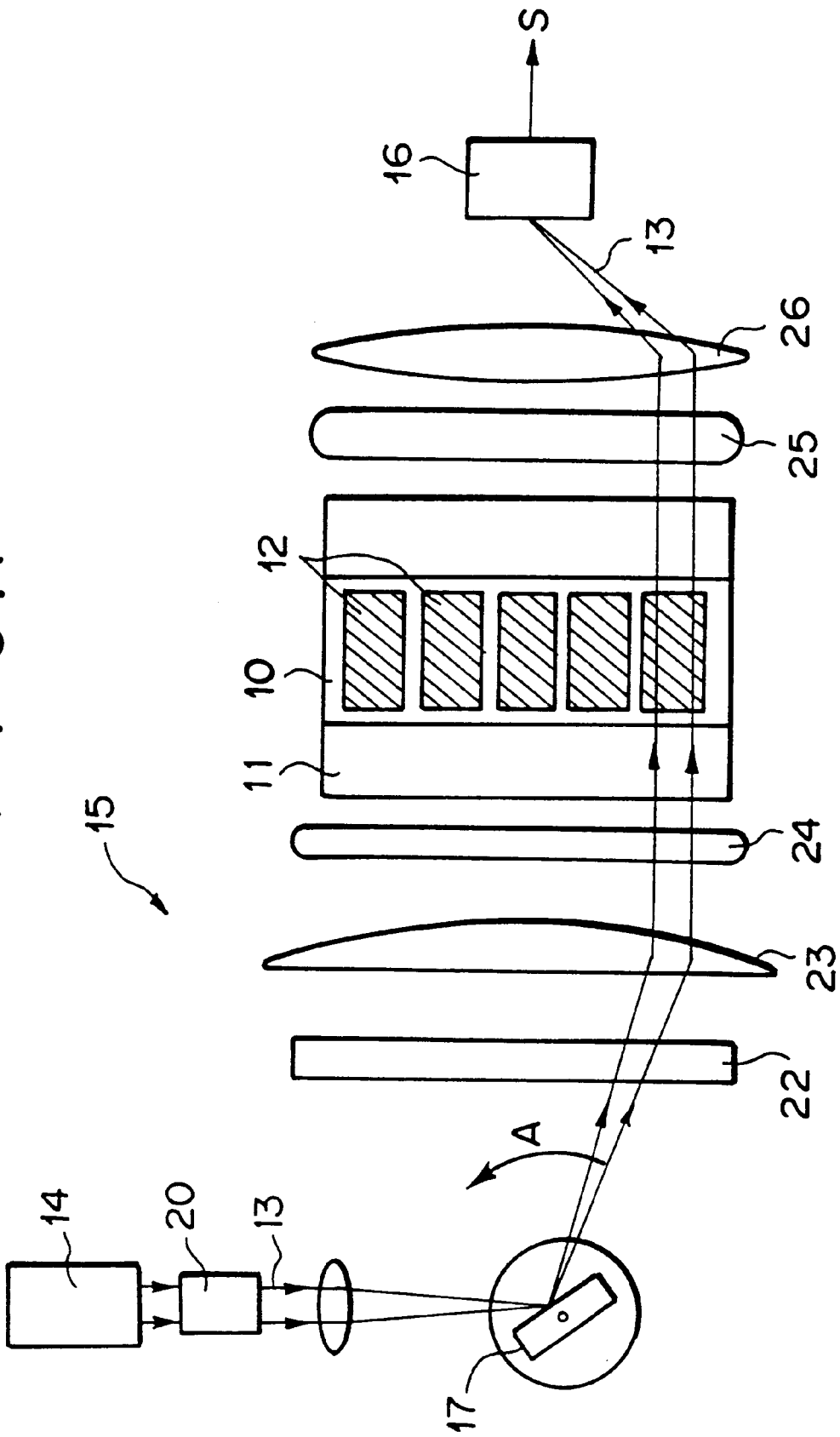
FIG. 1 is a plan view of a surface plasmon sensor in accordance with a first embodiment of the present invention.
Figure 2:
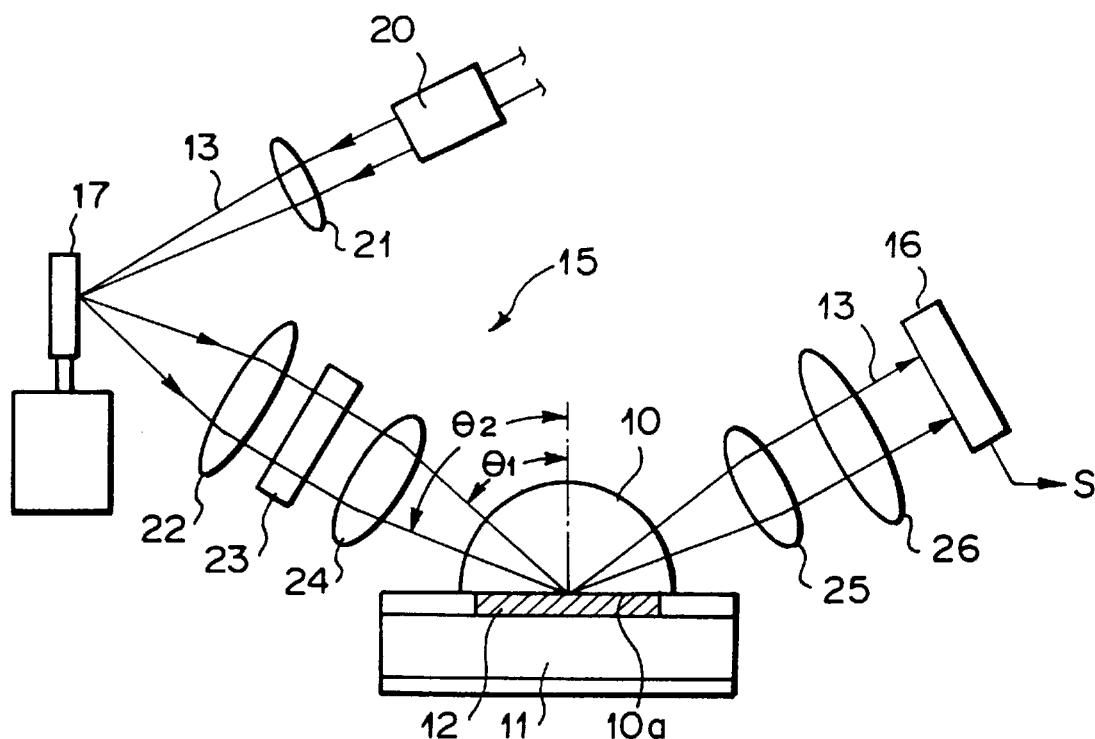
FIG. 2 is a side view of the surface plasmon sensor.

In FIGS. 1 and 2, a surface plasmon sensor in accordance with a first embodiment of the present invention comprises a semi-cylindrical prism 10, a plurality of (five in this particular embodiment) metal film pieces 12 such as of gold, silver or the like which are formed on one face (the lower face as seen in FIG. 2) of the prism 10 and are brought into contact with a plurality of samples 11, a light source 14 such as a semiconductor laser emitting a single light beam 13, an optical system 15 which causes the light beam 13 to enter the prism 10 so that various angles of incidence of the light beam 13 to the interface 10a between the prism 10 and the metal film pieces 12 can be obtained, a photodetector means 16 which detects the intensity of the light beam 13 reflected in total reflection from the interface 10a for the various angles of incidence and a galvanometer mirror 17 which deflects the light beam 13 in the direction of arrow A in FIG. 1.

The optical system 15 comprises a beam shaping optical system 20 for shaping the light beam 13, a condenser lens 21 which condenses the collimated light beam 13 on the mirror surface of the galvanometer mirror 17, three incident side cylindrical lenses 22, 23 and 24 which converge the diverging light beam 13 reflected from the mirror surface of the galvanometer mirror 17 only in a plane normal to the longitudinal axis of the prism 10, an emergent side cylindrical lens 25 which collimates the light beam 13 which is reflected in total reflection from the interface 10a in a diverging state in the plane normal to the longitudinal axis of the prism 10 and a condenser lens 26 which condenses the light beam 13 on a light receiving surface of the photodetector means 16.

Since the light beam 13 is converged on the interface 10a by the incident side cylindrical lenses 22, 23 and 24, the light beam 13 impinging upon the interface 10a contains components which impinge upon the interface 10a at various angles θ. In FIG. 2, θ1 denotes a minimum angle of incidence and θ2 denotes a maximum angle of incidence. The angle of incidence θ is made not smaller than an angle of total inner reflection. The light beam 13 is reflected in total reflection from the interface 10a and the reflected light beam 13 contains components which are reflected from the interface 10a at various angles.

The light receiving surface of the photodetector means 16 extends in such a direction that the whole components of the light beam 13 reflected from the interface 10a at various angles can be received by the light receiving surface. As the photodetector means 16, a CCD line sensor or the like may be used. Light detecting signals S output from the respective light receiving elements of the photodetector means 16 represent the intensities of the light beam 13 reflected at various angles, that is, for various angles of incidence.

Analysis of samples by the surface plasmon sensor of this embodiment will be described, hereinbelow.

That is, five samples 11 are placed in contact with the respective metal film pieces 12. The metal film pieces 12 may either be of the same metal or of different metals.

When effecting analysis, a light beam 13 is emitted from the light source 14 and the light beam 13 is first deflected by the galvanometer mirror 17 to converge on the lowermost (as seen in FIG. 1) metal film piece 12 through the cylindrical lenses 22, 23 and 24. The light beam 13 reflected in total reflection from the interface 10a between the lowermost metal film piece 12 and the prism 10 is detected by the photodetector means 16.

Figure 3:
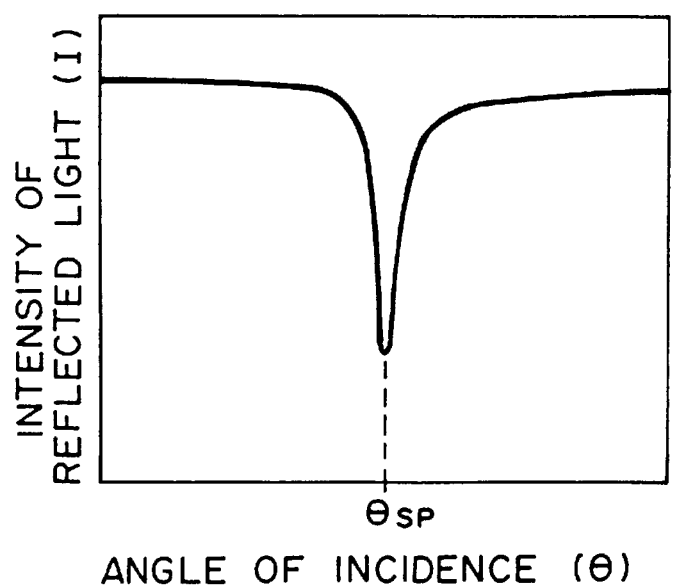
FIG. 3 is a graph showing the relation between the angle of incidence of a light beam and the output of the photodetector means.

As described above, the light detecting signals S output from the respective light receiving elements of the photodetector means 16 represent the intensities I of the reflected light beam 13 for the respective angles of incidence θ. The relation between the intensity I of the reflected light beam 13 and the angle of incidence θ is approximately as shown in FIG. 3.

As described in detail before, a light beam impinging upon the interface 10a at a particular angle of incidence θsp excites surface plasmon in the interface 10a, and the intensity I of the light reflected from the interface 10a at an angle corresponding to the angle θsp greatly drops. The particular angle of incidence θsp can be known from the light detecting signals S output from the light receiving elements of the photodetector means 16 and a specific material in the sample 11 can be quantitatively analyzed on the basis of the value of the particular angle of incidence θsp as described above.

The galvanometer mirror 17 is driven stepwise or continuously to deflect the light beam 13 in the direction of arrow A in FIG. 1, thereby projecting the light beam 13 onto the five film pieces 12 in sequence. In this manner, analyses of the five samples 11 are effected in sequence in a short time.

In the surface plasmon sensor of this embodiment, analyses in a plurality of channels are effected by use of a single light beam 13 and accordingly the amount of light beam does not fluctuate from channel to channel, which results in a high analyzing accuracy.

Further since a common light beam is used for a plurality of channels, the amount of light beam for each channel can be sufficient unlike the case where a single light beam is divided into a plurality of light beams, and the number of channels can be substantially increased.

Further since the light source emitting a single light beam is less expensive as compared with a light source emitting a plurality of light beams, the multiple channel surface plasmon sensor of this embodiment can be produced at lower cost than that using a light source emitting a plurality of light beams.

Further since the optical system 15 is provided with the incident side cylindrical lenses 22, 23 and 24, the emergent side cylindrical lens 25 and the condenser lens 26 which are arranged so that the light beam 13 reflected in total reflection from the interface 10a is condensed in a predetermined position irrespective of the deflecting angle, the photodetector means 16 may be one in number though the surface plasmon sensor of this embodiment is of a multiple channel type and accordingly the multiple channel surface plasmon of this embodiment can be produced at low cost.

Figure 4:
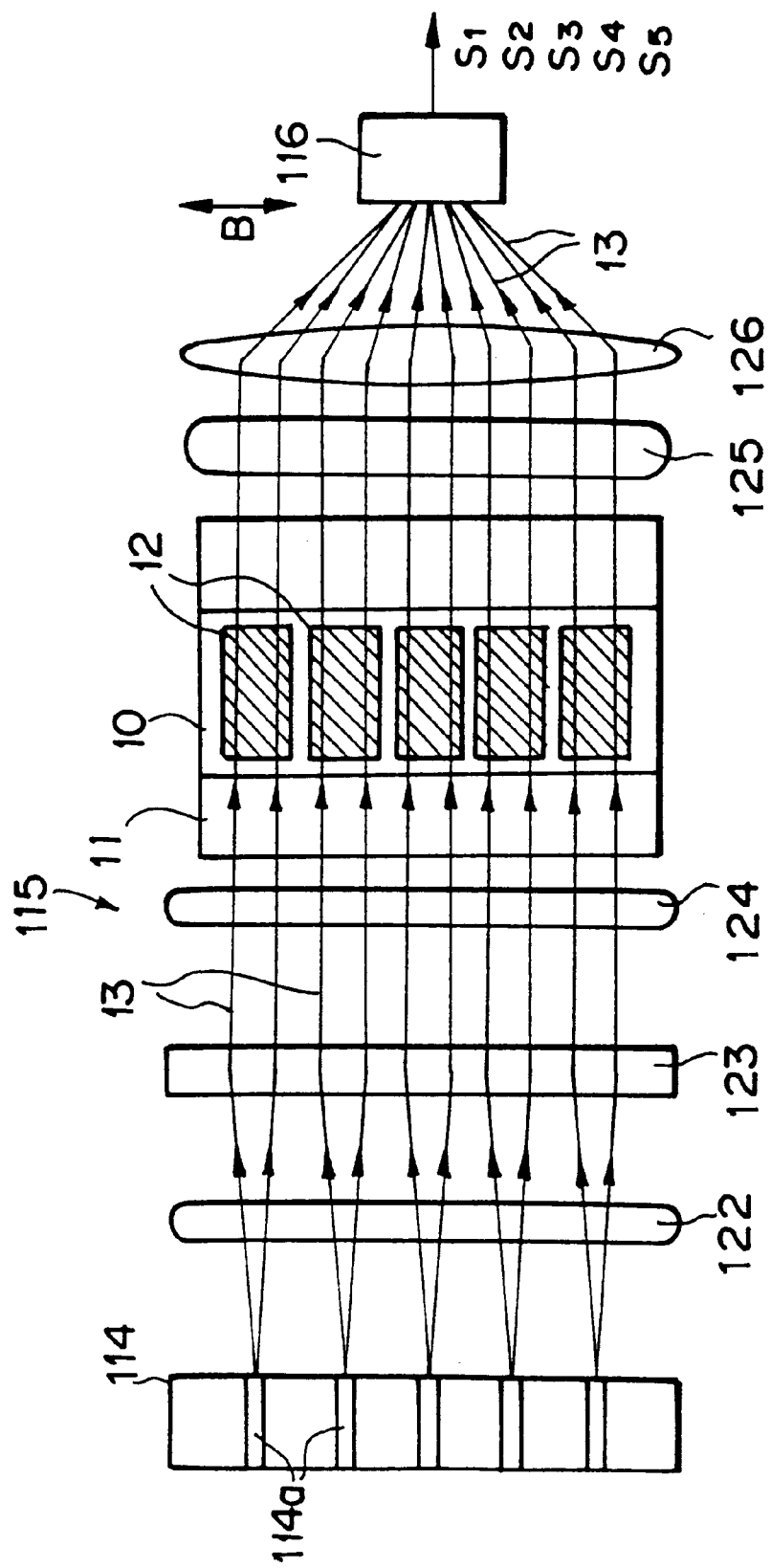
FIG. 4 is a plan view of a surface plasmon sensor in accordance with a second embodiment of the present invention.
Figure 5:
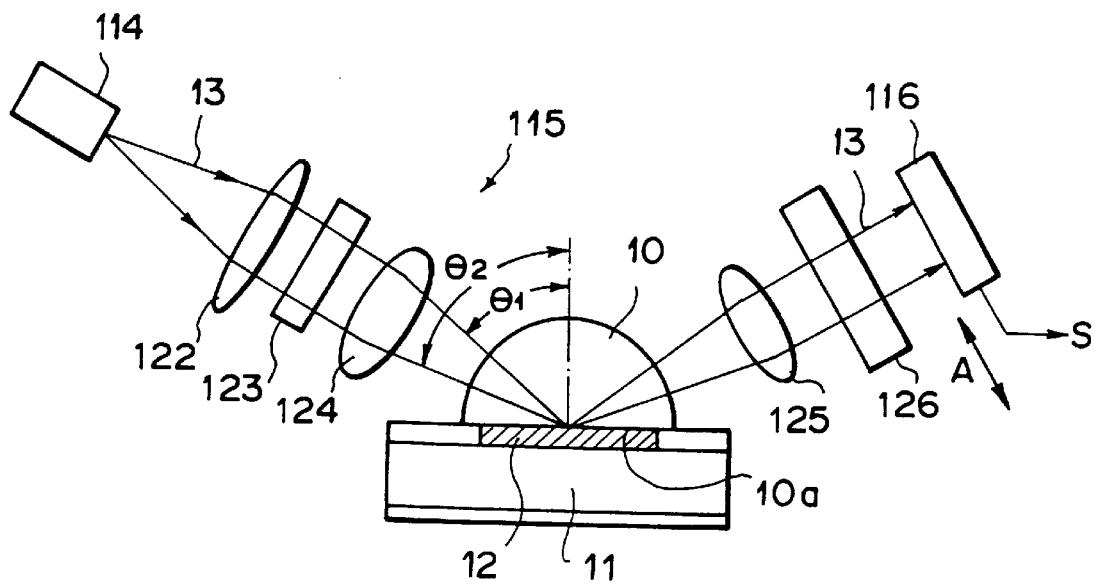
FIG. 5 is a side view of the surface plasmon sensor of the second embodiment.

A surface plasmon sensor in accordance with a second embodiment of the present invention will be described with reference to FIGS. 4 and 5, hereinbelow. In FIGS. 4 and 5, the elements analogous to those shown in FIGS. 1 and 2 are given the same reference numerals.

In FIGS. 4 and 5, the surface plasmon sensor in accordance with the second embodiment of the present invention comprises a semi-cylindrical prism 10, a plurality of (five in this particular embodiment) metal film pieces 12 such as of gold, silver or the like which are formed on one face (the lower face as seen in FIG. 5) of the prism 10 and are brought into contact with a plurality of samples 11, a semiconductor laser array 114 which has five light emitting portions (stripes) 114a each emitting a light beam 13, an optical system 115 which causes the light beam 13 emitted from each light emitting portion 114a to enter the prism 10 so that various angles of incidence of the light beam 13 to the interface 10a between the prism 10 and the metal film pieces 12 can be obtained for each light beam 13, a photodetector means 116 which detects the intensities of the light beams 13 reflected in total reflection from the interface 10a for the various angles of incidence.

The optical system 115 comprises a pair of incident side cylindrical lenses 122 and 124 which converge the diverging light beam 13 emitted from each light emitting portion 114a of the semiconductor laser array 114 only in a plane normal to the longitudinal axis of the prism 10, another incident side cylindrical lens 123 which collimates the light beam 13 in a plan view, an emergent side cylindrical lens 125 which collimates in a plan view the light beam 13 which is reflected in total reflection from the interface 10a in a diverging state in the plane normal to the longitudinal axis of the prism 10 and another emergent side cylindrical lens 126 which condenses the light beam 13 in a plan view. The cylindrical lens 126 condenses the five light beams 13 in different positions.

Since each light beam 13 is converged on the interface 10a by the incident side cylindrical lenses 122 and 124, each light beam 13 impinging upon the interface 10a contains components which impinge upon the interface 10a at various angles θ. In FIG. 5, θ1 denotes a minimum angle of incidence and θ2 denotes a maximum angle of incidence. The angle of incidence θ is made not smaller than an angle of total inner reflection. Each light beam 13 is reflected in total reflection from the interface 10a and the reflected light beam 13 contains components which are reflected from the interface 10a at various angles.

The photodetector means 116 has five arrays of light receiving elements. In each array, a plurality of light receiving elements are arranged in such a direction that the whole components of the light beam 13 reflected from the interface 10a at various angles can be received by the light receiving elements, that is, in the direction of arrow A in FIG. 5. The light receiving element arrays are arranged in the direction of arrow B in FIG. 4 and are respectively positioned in five positions in which the five light beams 13 are condensed by the cylindrical lens 126. As the photodetector means 116, a CCd area sensor or the like may be used.

Light detecting signals Sm (m=1, 2, 3, 4 and 5) output from the light receiving elements of the respective arrays represent the intensities of the respective light beams 13 and the light detecting signals output from the respective elements in each array represent the intensities of the light beam 13 reflected at various angles, that is, for various angles of incidence.

Analysis of samples 11 by the surface plasmon sensor of this embodiment will be described, hereinbelow.

That is, five samples 11 are placed in contact with the respective metal film pieces 12. The metal film pieces 12 may either be of the same metal or of different metals.

When effecting analysis, five light beams 13 are simultaneously emitted from the semiconductor laser array 114 and are converged on the respective metal film pieces 12 through the cylindrical lenses 122 and 124. The light beams 13 reflected in total reflection from the inerface 10a between the metal film pieces 12 and the prism 10 are detected by the photodetector means 116.

The analysis of each sample 11 is effected in the same manner as in the first embodiment and will not be described here.

In the surface plasmon sensor of this embodiment, five light beams 13 are simultaneously projected toward the five metal film pieces 12 and analyses of the five samples 11 are simultaneously effected, whereby analyses of five samples 11 can be effected in a short time at one time.

Further since the light beam 13 used in each channel is emitted from each of the light emitting portions 114a of the semiconductor laser array 114, a sufficient amount of light can be ensured for each of the channels, unlike the case where the light beam used in each channel is obtained by dividing a single light beam into a plurality of light beams, whereby a high analyzing accuracy can be obtained.

The semiconductor laser array 114 may be driven so that the light emitting portions 114a emit light in sequence at time intervals. In this case, by arranging the optical system 115 so that the light beam 13 reflected in total reflection from the interface 10a is condensed in a predetermined position irrespective of from which light emitting portion 114a the light beam 13 is emitted, the photodetector means 116 may be simple in structure, that is, the photodetector means 116 may have only a single array of light detecting elements.

What is claimed is:

1. A surface plasmon sensor, comprising:
    a prism,
    a plurality of metal films which are formed on one face of the prism and are side by side and brought into contact with a plurality of areas on a plurality of samples,
    a light source emitting a light beam,
    an optical system which causes the light beam to enter the prism so that various angles of incidence of the light beam to the interface between the prism and the plurality of metal films can be obtained,
    a photodetector means which is able to detect the intensity of the light beam reflected in total reflection from the interface for the various angles of incidence, and
    a light deflector means which deflects the light beam at an unvaried angle of incidence so that the light beam converges and impinges upon the interface between the prism and the plurality of metal films in a plurality of different positions in sequence.

2. The surface plasmon sensor as defined in claim 1 in which the optical system is arranged so that the light beam reflected in total reflection from the interface between the prism and the plurality of metal films is condensed in a predetermined position irrespective of the position where the incident light beam impinges upon the interface.

3. A surface plasmon sensor, comprising:
    a prism,
    a plurality of metal films which are formed on one face of the prism and are side by side and brought into contact with a plurality of areas on a plurality of samples,
    a semiconductor laser array which has a plurality of light emitting portions each emitting a light beam,
    an optical system which causes the light beams emitted from the semiconductor laser array to converge and enter the prism so that various angles of incidence to the interface between the prism and the plurality of metal films can be obtained for each of the light beams, and
    a photodetector means which is able to detect the intensity of the light beam reflected in total reflection from the interface for the various angles of incidence of each of the light beams.

4. The surface plasmon sensor as defined in claim 3 in which
    the semiconductor laser array is driven so that light beams are emitted simultaneously from the light emitting portions of the semiconductor laser array,
    the optical system is arranged to condense the plurality of light beams reflected from the interface between the prism and the plurality of metal films in different positions, and
    the photodetector means has a plurality of light receiving portions each of which discretely receives one of the condensed light beams.

5. The surface plasmon sensor as defined in claim 3 in which
    the semiconductor laser array is driven so that light beams are emitted in sequence from the light emitting portions of the semiconductor laser array at time intervals,
    the optical system is arranged to condense the plurality of light beams reflected from the interface between the prism and the plurality of metal films in the same position and
    the photodetector means has a light receiving portion common to the plurality of the condensed light beams.

6. The surface plasmon sensor as defined in claim 2, wherein said photodetector means is a CCD line sensor.

7. The surface plasmon sensor as defined in claim 4, wherein said photodetector means is a CCD area sensor.

8. The surface plasmon sensor as defined in claim 5, wherein said photodetector means is a CCD line sensor.

* * * * *